United States Patent
Dyer et al.

(10) Patent No.: US 9,297,638 B1
(45) Date of Patent: Mar. 29, 2016

(54) TWO-PATH PLASMONIC INTERFEROMETER WITH INTEGRATED DETECTOR

(71) Applicants: Sandia Corporation, Albuquerque, NM (US); Gregory Aizin, East Brunswick, NJ (US)

(72) Inventors: Gregory Conrad Dyer, Albuquerque, NM (US); Eric A. Shaner, Rio Rancho, NM (US); Gregory Aizin, East Brunswick, NJ (US)

(73) Assignees: Sandia Corporation, Albuquerque, NM (US); Research Foundation of The City of New York, New York, NY (US)

( * ) Notice: Subject to any disclaimer, the term of this patent is extended or adjusted under 35 U.S.C. 154(b) by 0 days.

(21) Appl. No.: 14/520,057

(22) Filed: Oct. 21, 2014

(51) Int. Cl.
  *G01J 5/02* (2006.01)
  *G01B 9/02* (2006.01)

(52) U.S. Cl.
  CPC ........ *G01B 9/02001* (2013.01); *G01B 9/02049* (2013.01)

(58) Field of Classification Search
  CPC . G02F 2203/10; G02F 1/0316; G02B 6/1225; G02B 2006/12159; G02B 6/1226; G02B 9/02001; G02B 9/02049
  USPC ....................................................... 250/353
  See application file for complete search history.

(56) References Cited

U.S. PATENT DOCUMENTS

| | | | | |
|---|---|---|---|---|
| 5,856,681 | A | * | 1/1999 | Ohshima ............. H01L 29/1029 257/194 |
| 7,376,403 | B1 | * | 5/2008 | Wanke .................. H01L 29/205 257/19 |

(Continued)

OTHER PUBLICATIONS

W.F. Andress et al., "Ultra-Subwavelength Two-Dimensional Plasmonic Circuits", Nano Letters, vol. 12 (2012), pp. 2272-2277.

(Continued)

*Primary Examiner* — David J Makiya
*Assistant Examiner* — Taeho Jo
(74) *Attorney, Agent, or Firm* — Kevin W. Bieg

(57) ABSTRACT

An electrically tunable terahertz two-path plasmonic interferometer with an integrated detection element can down convert a terahertz field to a rectified DC signal. The integrated detector utilizes a resonant plasmonic homodyne mixing mechanism that measures the component of the plasma waves in-phase with an excitation field that functions as the local oscillator in the mixer. The plasmonic interferometer comprises two independently tuned electrical paths. The plasmonic interferometer enables a spectrometer-on-a-chip where the tuning of electrical path length plays an analogous role to that of physical path length in macroscopic Fourier transform interferometers.

20 Claims, 11 Drawing Sheets

(56) References Cited

U.S. PATENT DOCUMENTS

| | | | | |
|---|---|---|---|---|
| 7,420,225 | B1* | 9/2008 | Wanke | B82Y 10/00 257/184 |
| 7,619,263 | B2* | 11/2009 | Shur | H01S 1/02 257/198 |
| 7,705,415 | B1* | 4/2010 | Nabet | H01L 31/1035 257/443 |
| 8,274,058 | B1* | 9/2012 | Wanke | B82Y 20/00 250/370.12 |
| 8,304,812 | B2* | 11/2012 | Onishi | H01L 29/0692 257/184 |
| 8,755,648 | B1* | 6/2014 | Sayyah | G02F 1/025 385/30 |
| 8,940,147 | B1* | 1/2015 | Bartsch | G01N 27/44791 204/601 |
| 9,105,791 | B1* | 8/2015 | Dyer | H01L 31/1127 |
| 2005/0099345 | A1* | 5/2005 | von Klitzing | B82Y 20/00 343/703 |
| 2006/0081889 | A1* | 4/2006 | Shur | G02B 6/10 257/221 |
| 2007/0194225 | A1* | 8/2007 | Zorn | B82Y 35/00 250/306 |
| 2009/0267646 | A1* | 10/2009 | De Los Santos | H01L 49/006 326/46 |
| 2011/0031378 | A1* | 2/2011 | Hirose | H01L 31/10 250/208.1 |
| 2011/0102068 | A1* | 5/2011 | Bouchiat | G01N 27/4146 327/527 |
| 2011/0204418 | A1* | 8/2011 | Onishi | H01L 29/0692 257/194 |
| 2012/0061728 | A1* | 3/2012 | Javey | H01L 21/2007 257/192 |
| 2013/0018599 | A1* | 1/2013 | Peng | B82Y 15/00 702/30 |
| 2013/0277716 | A1* | 10/2013 | Otsuji | H01L 29/42316 257/252 |
| 2014/0197896 | A1* | 7/2014 | Ouchi | H03B 7/08 331/107 T |
| 2015/0109606 | A1* | 4/2015 | Peale | H01L 31/1136 356/30 |

OTHER PUBLICATIONS

K.Y.M. Yeung et al. "Two-Path Solid-State Interferometry Using Ultra-Subwavelength Two-Dimensional Plasmonic Waves", Applied Physics Letters 102 (2013), pp. 021104-1-021104-4.

S. Rosenblatt et al., "Mixing at 50 GHz Using a Single-Walled Carbon Nanotube Transistor", Applied Physics Letters 87 (2005), pp. 153111-1-153111-3.

V.M. Muravev et al., "Plasmonic Detector/Spectrometer of Subterahertz Radiation Based on Two-Dimensional Electron System with Embedded Defect", Applied Physics Letters 100 (2012), pp. 082102-1-082102-3.

G.C. Dyer et al., "A Terahertz Plasmon Cavity Detector", Applied Physics Letters 97 (2010), pp. 193507-1-193507-3.

G.C. Dyer et al., "Enhanced Performance of Resonant Sub-Terahertz Detection in a Plasmonic Cavity", Applied Physics Letters 100 (2012), pp. 083506-1-083506-4.

G.C. Dyer et al., "Inducing an Incipient Terahertz Finite Plasmonic Crystal in Coupled Two Dimensional Plasmonic Cavities", Physical Review Letters 109 (2012), pp. 126803-1-126803-5.

G.C. Dyer et al., "Induced Transparency by Coupling of Tamm and Defect States in Tunable Terahertz Plasmonic Crystals", Nature Photonics, vol. 7 (2013), pp. 925-930.

* cited by examiner

FIG. 7(a) 0.270 THz
FIG. 7(b) 0.330 THz

TWO-PATH PLASMONIC INTERFEROMETER WITH INTEGRATED DETECTOR

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to widely voltage tunable far- and mid-infrared plasmonic devices and, in particular, to a two-path plasmonic interferometer with an integrated detector.

BACKGROUND OF THE INVENTION

There has been significant recent interest in the development of terahertz (THz) integrated circuits (ICs) and detectors based upon two-dimensional electron gas (2DEG) systems in semiconductor nanostructures and graphene. Because microwave and THz fields coupled to a 2DEG excite plasma waves, plasmon-based field-effect devices can operate well above $f_T$, the cutoff frequency determined by carrier transit times. See M. I. Dyakonov and M. S. Shur, *Phys. Rev. Lett.* 71, 2465 (1993); M. I. Dyakonov and M. S. Shur, *IEEE Trans. on Electron Devices* 43, 380 (1996); W. F. Andress et al., *Nano Lett.* 12, 2272 (2012); P. J. Burke et al., *Appl. Phys. Lett.* 76, 745 (2000); and M. J. W. Rodwell et al., *IEEE Trans. on Electron Devices* 48, 2606 (2001). Overdamped plasmonic field-effect transistors (FETs) have been fabricated from III-V, Si, and graphene material systems and utilized for room temperature THz detection. See D. Coquillat et al., *Opt. Express* 18, 6024 (2010); S. Preu et al., *IEEE Trans. on THz Sci. and Tech.* 2, 278 (2012); M. S. Vitiello et al., *Nano Lett.* 12, 96 (2011); A. D. Gaspare et al., *Appl. Phys. Lett.* 100, 203504 (2012); A. Pitanti et al., *Appl. Phys. Lett.* 101, 141103 (2012); A. Lisauskas et al., *J. Appl. Phys.* 105, 114511 (2009); S. Boppel et al., *Electronics Letters* 47, 661 (2011); and L. Vicarelli et al., *Nature Mater.* 11, 865 (2012). To exploit underdamped two-dimensional (2D) plasmons in III-V heterostructures, cryogenic operation of a high-electron-mobility-transistor (HEMT) is generally required. See W. F. Andress et al., *Nano Lett.* 12, 2272 (2012); P. J. Burke et al., *Appl. Phys. Lett.* 76, 745 (2000); X. G. Peralta et al., *Appl. Phys. Lett.* 81, 1627 (2002); E. A. Shaner et al., *Appl. Phys. Lett.* 87, 193507 (2005); W. Knap et al., *Appl. Phys. Lett.* 81, 4637 (2002); and V. M. Muravev and I. V. Kukushkin, *Appl. Phys. Lett.* 100, 082102 (2012). Within this constraint, potential applications such as THz plasmonic ICs and detectors based on III-V heterostructures can be realized in these material systems. However, as the quality of large-area graphene materials improves, similar devices may emerge that operate in the mid-infrared at room temperature.

SUMMARY OF THE INVENTION

The present invention is directed to a two-path plasmonic interferometer, comprising a layer providing a two-dimensional electron gas (2DEG) or two-dimensional hole gas (2DHG); a source and a drain at opposing ends of the 2DEG or 2DHG layer; a source-side gate, a central gate, and a drain-side gate disposed on and separated from the 2DEG or 2DHG layer; and a voltage source for applying a voltage independently to each of the gates to spatially modulate the electron or hole density in the 2DEG or 2DHG layer under each gate, thereby providing a source-side plasmonic path under the source-side gate and a drain-side plasmonic path under the drain-side gate and a plasmonic mixer under the central gate when the central gate is biased to near depletion; wherein a standing plasma wave from the source-side plasmonic path couples with a standing plasma wave from the drain-side plasmonic path interfere at the plasmonic mixer to provide a photoresponse when incident electromagnetic radiation is coupled to the 2DEG or 2DHG layer.

The incident electromagnetic radiation can have a frequency of between 10 GHz and 60 THz (i.e., free space wavelength of between 30 mm and 5 µm). The length of the source-side and drain-side plasmonic paths can each be less than $^{1}/_{10}$ the free space wavelength of the incident electromagnetic radiation and can have equal plasmonic lengths. A sample can be placed in one of the balanced plasmonic paths to enable interferometric spectroscopy of the sample. An antenna and/or a hyper-hemispherical lens can couple the incident electromagnetic radiation to the 2DEG or 2DHG layer. Alternatively, the incident electromagnetic radiation can be coupled into the 2DEG or 2DHG layer via on-chip waveguides. When used as a homodyne mixer, the photoresponse is a rectified DC voltage signal measured between the source and the drain terminals. The voltages to the source-side and drain-side gates can be varied to obtain an interofergram from the rectified DC signal. The interferogram can be post-processed to provide a frequency domain spectrum of the incident electromagnetic spectrum. Alternatively, the two-path plasmonic interferometer can be used as a heterodyne mixer by applying a local oscillator signal to the plasmonic mixer that has a frequency detuned from the incident electromagnetic radiation, thereby providing an intermediate frequency difference signal.

BRIEF DESCRIPTION OF THE DRAWINGS

The detailed description will refer to the following drawings, wherein like elements are referred to by like numbers.

calculated using the channel conductance measured at 8 K, as a function of voltage applied to G1.

plotted as a function of voltage $V_{Gj}$ applied to gates G1, G2, and G3, calculated using the channel conductance measured at 8 K of the HEMT illustrated in FIG. 3.

FIGS. 7(a) and 7(b) are plots of the photoresponse under 0.270 THz and 0.330 THz excitation at 8 K, respectively, as a function of the electrical lengths of Path S, $\theta_S$, and Path D, $\theta_D$, with G2 defining the mixing region of the HEMT as illustrated in FIG. 3(a).

DETAILED DESCRIPTION OF THE INVENTION

The present invention is directed to a two-dimensional (2D) plasmonic interferometer with an integrated resonant homodyne mixing element based upon a HEMT with multiple gate terminals. Biasing a gate in a HEMT near its threshold voltage while illuminated by radiation near the 2D plasma frequency effectively produces a plasmonic homodyne mixing element and enables phase sensitive detection of plasma waves. When multiple plasmonic cavities are coupled to this gate-induced plasmonic mixing element, the device can provide a sub-wavelength two-path interferometer with an integrated on-chip detector where the paths can be independently tuned. See W. F. Andress et al, *Nano Lett.* 12, 2272 (2012); and K. Y. M. Yeung et al., *Appl. Phys. Lett.* 102, 021104 (2013). Unlike standard homodyne mixing techniques, plasmonic homodyne mixing permits near-field detection well above the conventional RC-limited bandwidth of devices at their operational bias. See S. Rosenblatt et al., *Appl. Phys. Lett.* 87, 153111 (2005).

To describe the underlying mechanism of the solid-state plasmonic interferometer of the present invention, it is useful to first draw an analogy to an optical Mach-Zehnder interferometer. An optical Mach-Zehnder interferometer can be used to determine the relative phase shift variations between two collimated beams derived by splitting light from a single source. An optical Mach-Zehnder interferometer, comprising optical Path D and optical Path S, is diagrammed in FIG. 1. Beam splitters are labeled BS1 and BS2 and mirrors are labeled MD and MS. Each optical path has a region of length d where the permittivity ($\epsilon_D$, $\epsilon_S$) and permeability ($\mu_D$, $\mu_S$) of the electromagnetic medium is independently defined. If the phase velocity in these regions is given by $v_{D,S}=1/\sqrt{\epsilon_{D,S}\mu_{D,S}}$, then the phase difference of beams on these two paths is $\theta_D-\theta_S=\omega d(v_D^{-1}-v_S^{-1})$. This phase difference results not from a difference in path lengths (i.e., $\Delta d=0$), but instead from a difference in the phase velocities along sections of the two paths (i.e., $v_D \neq v_S$). When the permittivity, permeability, or both, are tunable, then so are the phase velocities $v_{D,S}$ of these regions and consequently the phase difference $\theta_D-\theta_S$ between the two paths. For example, the Mach-Zehnder interferometer can be used to measure phase shifts between the two split beams caused by a sample that modifies the permittivity and/or permeability in one of the optical paths. Readout in this diagram can be accomplished using a mixer to produce a DC signal at the second beamsplitter BS2 where the recombined beams are 180 degrees out of phase.

Figure 2A:
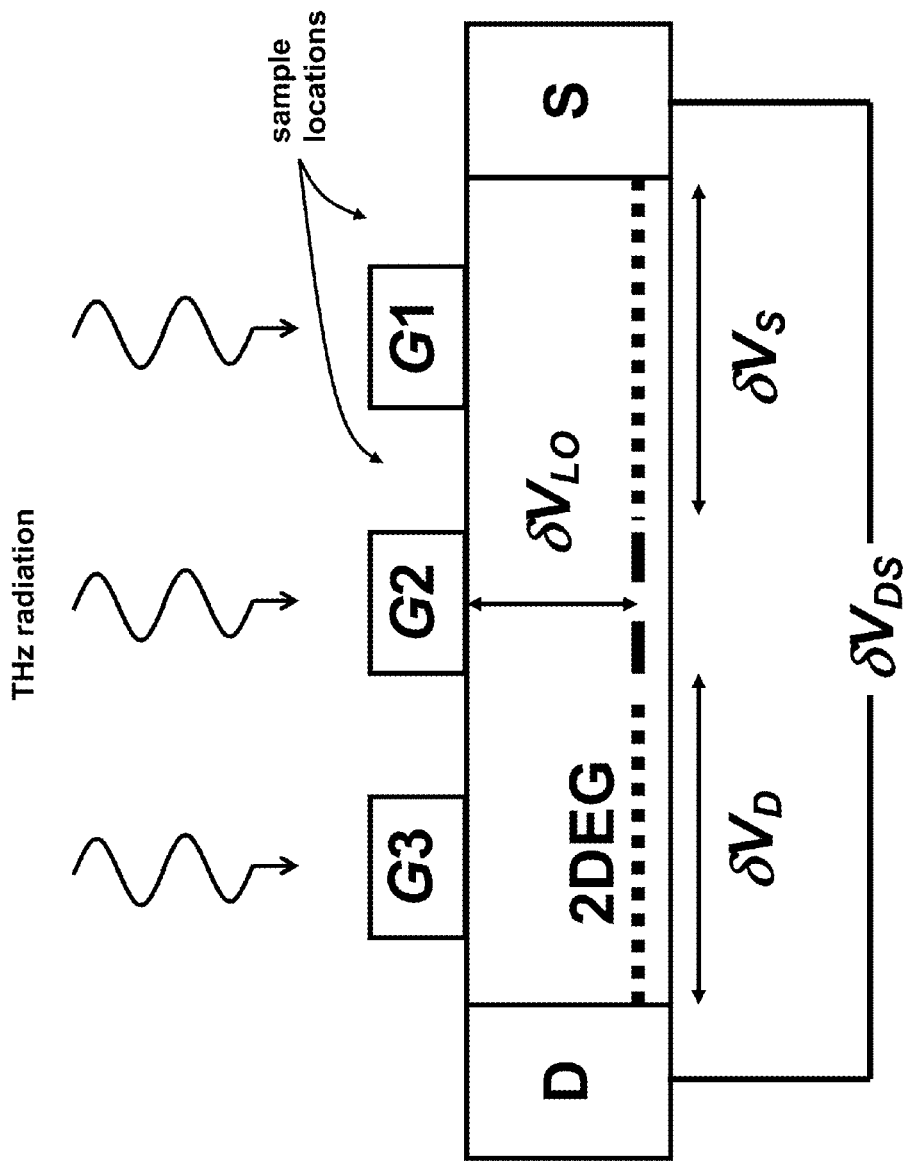
FIG. 2(a) is a side-view schematic illustration of a subwavelength plasmonic interferometer with integrated detector.

FIG. 2(a) is a schematic side-view illustration of a sub-wavelength plasmonic interferometer with integrated detector of the present invention. The interferometer is based upon a high-mobility two-dimensional electron gas (2DEG) or two-dimensional hole gas (2DHG). A 2DEG is used for simplicity to describe the invention below, but the concepts apply similarly to a 2DHG. The 2DEG can be a layer comprising a gas of electrons free to move in two dimensions, but tightly confined in the third dimension. For example, the 2DEG layer can comprise a semiconductor heterojunction or an atomically thin material having high electron mobility formed on a substrate or as a suspended membrane. A source-side gate G1, a center gate G2, and a drain-side gate G3 are disposed on and separated from the 2DEG layer by a thin spacer layer. For example, the gates G1, G2, and G3 can be separated from the 2DEG layer by a semiconducting or insulating layer. Each of the gates G1, G2, and G3 can comprise one or more parallel finger electrodes. A voltage can be applied to a gate to spatially modulate the electron density in the 2DEG layer underlying the gate. A source S and a drain D can be formed at the opposing ends of the 2DEG layer to provide electrical contact to the structure. For interferometric applications, the gaps between metallic terminals, e.g. between S and G1 and G1 and G2, may be filled with a sample material. A potential location of sample placement is indicated in FIG. 2(a) by arrows. Just as the gates above the 2DEG layer modify plasmon propagation by screening effects, 2D plasmons are sensitive to other changes in local environment.

In a typical HEMT design, the drain D and source S contact are designed to provide conductive, low resistance electrical contact between the fabricated metal electrodes and the 2DEG. This follows the accepted naming convention of D and S contacts used for field effect transistors. However, D and S are more broadly applied in the present invention. D and S imply a preferential flow of electrical current through the 2DEG, while in the present invention there is no applied electrical current required for operation. Additionally, D and S can apply to non-conductive contacts at the end of the 2DEG in the context of this invention.

The integrated detector is a plasmonic mixing element. This mixing element can comprise a region of 2DEG with reduced or fully depleted 2DEG. See U.S. Pat. No. 7,376,403 to Wanke et al., which is incorporated herein by reference. When no electrical current is passed through the 2DEG, this detector functions as a plasmonic homodyne mixer. However, integration of an extrinsic mixing element such as a Schottky diode with a semiconductor heterojunction device is also possible. See U.S. Pat. No. 8,274,058 to Wanke et al., which is incorporated herein by reference. The underlying requirement is that the near field of the plasma excitations couples with the integrated mixer. Device-specific implementation can vary provided this requirement is satisfied.

A 2DEG can be formed at a heterojunction between two semiconductors having different band gaps. The heterojunction can comprise a wide-bandgap semiconductor heavily doped with an electron donor, such as n-type AlGaAs or n-type AlGaN, and an undoped narrow bandgap semiconductor, such as GaAs or GaN. For example, the heterojunction can be fabricated using molecular beam epitaxy. A semiconductor heterojunction is preferably grown on a semi-insulating and atomically flat substrate. The heterojunction thereby forms a quantum well in the conduction band of the undoped semiconductor. Electrons from the n-type semiconductor drop into the quantum well and can move with high mobility without colliding with impurities in the undoped semiconductor. A thin layer comprising highly mobile conducting electrons with very high concentration—the 2DEG—is thereby created at the heterojunction. Other III-V heterojunctions can also be used, including but not limited to GaAs/AlGaAs, InGaAs/InAlAs, and GaN/AlGaN.

Alternatively, a quantum well formed in a narrow gap semiconductor placed between wide gap semiconductors with remote n-type dopants can similarly provide a suitable 2DEG. Multiple quantum wells can also be employed to increase the total 2DEG density through summation of the densities in adjacent wells. Choice of the type of heterojunction or quantum well can impact 2DEG mobility and density as well as the depth of the well relative to the surface or the epitaxial growth. The depth of the embedded 2DEG layer ultimately determines the strength of plasmon screening due to fabricated metal terminals. Finally, type-II heterojunctions, such as those formed between InAs/GaSb, can produce a 2DEG which will differ greatly in majority carrier effective mass.

A 2DEG can also be formed in atomically thin materials having high electron mobility, such as graphene. Graphene is a one-atom thick layer of $sp^2$-bonded carbon arranged in a regular hexagonal pattern. As such, graphene can be considered as an indefinitely large polycyclic aromatic hydrocarbon in which electrons are free to move by virtue of the $sp^2$ bonding. In particular, graphene has been found to have remarkably high electron mobility at room temperature due to the low defect scattering of intrinsic graphene.

Alternatively, a two-dimensional hole gas (2DHG) having similar properties to the 2DEG but with positive carrier charge polarity can also be formed by chemical or electronic doping of graphene or in heterojunction-based materials. See U.S. Pat. No. 9,105,791, issued Aug. 11, 2015, which is incorporated herein by reference.

The incident radiation can have a frequency between about 10 GHz and 60 THz (i.e., free space wavelength of between 30 mm and 5 µm). All three gates G1, G2, and G3 can be driven by the incident electromagnetic radiation field. To achieve a two-path interferometer, gate G2 can be biased to depletion. Gates G1 and G3 then control independent source-side and drain-side paths for plasmonic standing waves to couple into the depleted region below G2.

The source-side and drain-side plasmonic path lengths are each shorter than a plasmon coherence length. A transmission line model, as described in U.S. Pat. No. 9,105,791, can be adapted to include plasmon damping by accounting for dissipation in the definitions of the transmission line characteristic impedance and dispersion. For calculating the plasmon Q-factor and propagation lengths, it is sufficient to define the dispersion law as $$q = -i\sqrt{i\omega C(i\omega L + R)}$$

where R accounts for the damping of the plasma wave. This resistance includes not only the scattering rate found from the Drude conductivity of the 2DEG, but also a radiative damping contribution. For high mobility 2DEGs ($\mu_{mob} > 100{,}000 \text{ cm}^2/\text{Vs}$), this radiation resistance is a more significant damping mechanism than the intrinsic 2DEG resistance. See S. A. Mikhailov, Phys. Rev. B 54, 10335 (1996). The total resistance can be defined in terms of the mobility and radiative scattering rates as, $$R = \frac{m^*}{\omega e^2 n_{2D}} (\tau_{mob}^{-1} + \tau_{rad}^{-1})$$

where $$\tau_{mob}^{-1} = \frac{e}{m^* \mu_{mob}}$$

and $$\tau_{rad}^{-1} = \sqrt{\frac{\mu_0}{\varepsilon}} \frac{e^2 n_{2DEG}}{2m^*}.$$

Using only fundamental constants and known or measured quantities (2DEG density, mobility, GaAs permittivity, carrier effective mass), the resistance R can be calculated explicitly to estimate the effects of dissipation upon the plasma wave.

To determine the plasmon Q-factor and propagation length from the dispersion law defined above, it is convenient to rewrite the dispersion law as $$q = \beta + i\alpha.$$

Then the Q-factor can be defined as, $$Q = \frac{\beta}{2\alpha}$$

with the propagation length of the damped plasmon subsequently given by, $$L_p = \frac{Q}{\beta} = \frac{1}{2\alpha}.$$

Both the Q-factor and propagation length relate to power dissipation of the plasmon. For examining coherent coupling effects, it is the coherence length that provides the more salient figure of merit. The coherence length is twice the propagation length, $$L_C = \frac{1}{\alpha}.$$

Figure 10B:
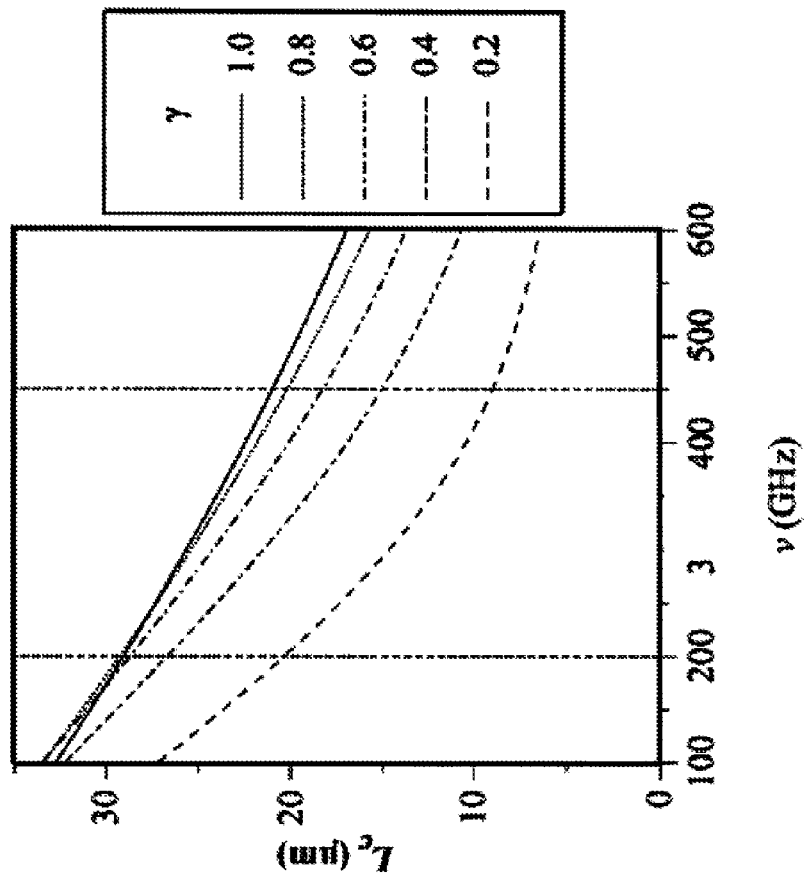
FIG. 10(b) is a graph of the coherence length.
Figure 10A:
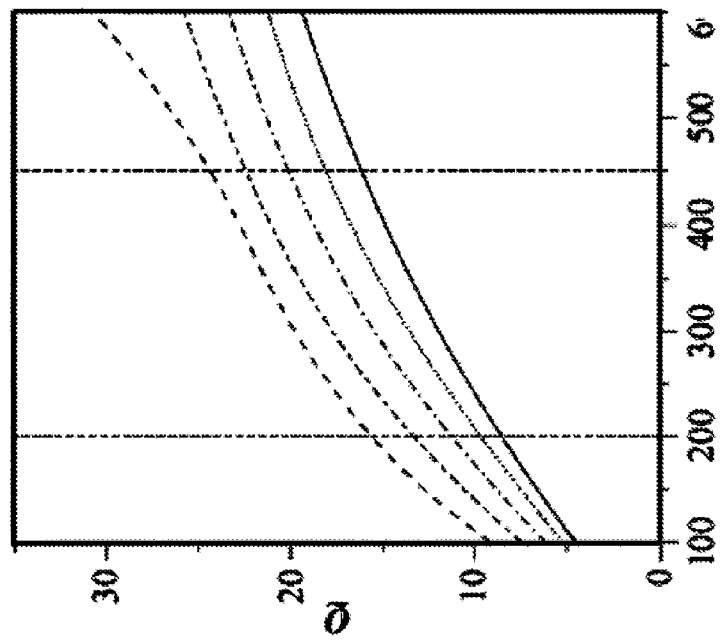
FIG. 10(a) is a graph of Q-factor of the plasmon as a function of frequency at five different normalized 2DEG densities for an exemplary GaAs/AlGaAs double quantum well heterostructure.

Tuning of the gate voltages G1 and G3 controls the 2DEG inductance and resistance, $L_j, R_j \propto 1\gamma_j$. Here $\gamma_j$ defines the normalized 2DEG density under the $j^{th}$ gate in terms of the threshold voltage $V_{th}$ (where $n_{2DEG} \rightarrow 0$) and the applied gate voltages $V_{Gj}$ such that $\gamma_j \equiv (V_{th} - V_{Gj})/V_{th}$. In FIGS. 10(a) and 10(b), respectively the plasmon Q-factor and coherence length $L_C$ calculated for a gated GaAs/AlGaAs 2DEG (with carrier density of about $4 \times 10^{11}$ cm$^{-2}$ at 12 K) are plotted as a function of frequency $\nu$ for several values of the normalized carrier density $\gamma$. The Q-factor of the plasma wave is approximately 10-25 in the range of frequencies from 200-450 GHz, shown with vertical dashed lines, and increases modestly as the normalized 2DEG density is lowered. The coherence length, however, depends much more critically on both the normalized 2DEG density and frequency. In this frequency range, the plasmon coherence length varies from $L_C < 30$ µm when $\gamma = 1$ (no applied gate voltage to $L_C < 20$ µm when $\gamma = 0.2$.

The depleted region below G2 functions as a plasmonic mixer in which the standing plasma waves coupled from its left and right 'ports' effectively interfere. The incident THz field coupled directly to G2 behaves as a local oscillator voltage $\delta V_{LO}$ while the plasma waves from below G1 and G3 act as signals $\delta V_S$ and $\delta V_D$ coupled to the mixer. The resultant homodyne mixing mechanism 'down converts' the THz fields to a DC signal $\delta V_{DS}$ that can be read out through the drain D and source S contacts. Not only does this down conversion turn high frequency fields into a DC signal easily transmitted on standard coax, but, for example, it can take place in a 10 micrometer long interferometer element that is 100× smaller than the mm-wavelength of THz radiation in free space. With two balanced paths, it is possible to perform interferometric spectroscopy on-chip, analogous to a Fourier transform infrared spectrometer. However, rather than mechanically tuning the path length of a traditional optical interferometer, the effective permittivity of the 2DEG interferometer paths can be changed by electrically tuning the gate voltages of G1 and G3. Post processing after measuring the interferogram (an FFT with other corrections) can provide a frequency domain spectrum of incident radiation.

Figure 2B:
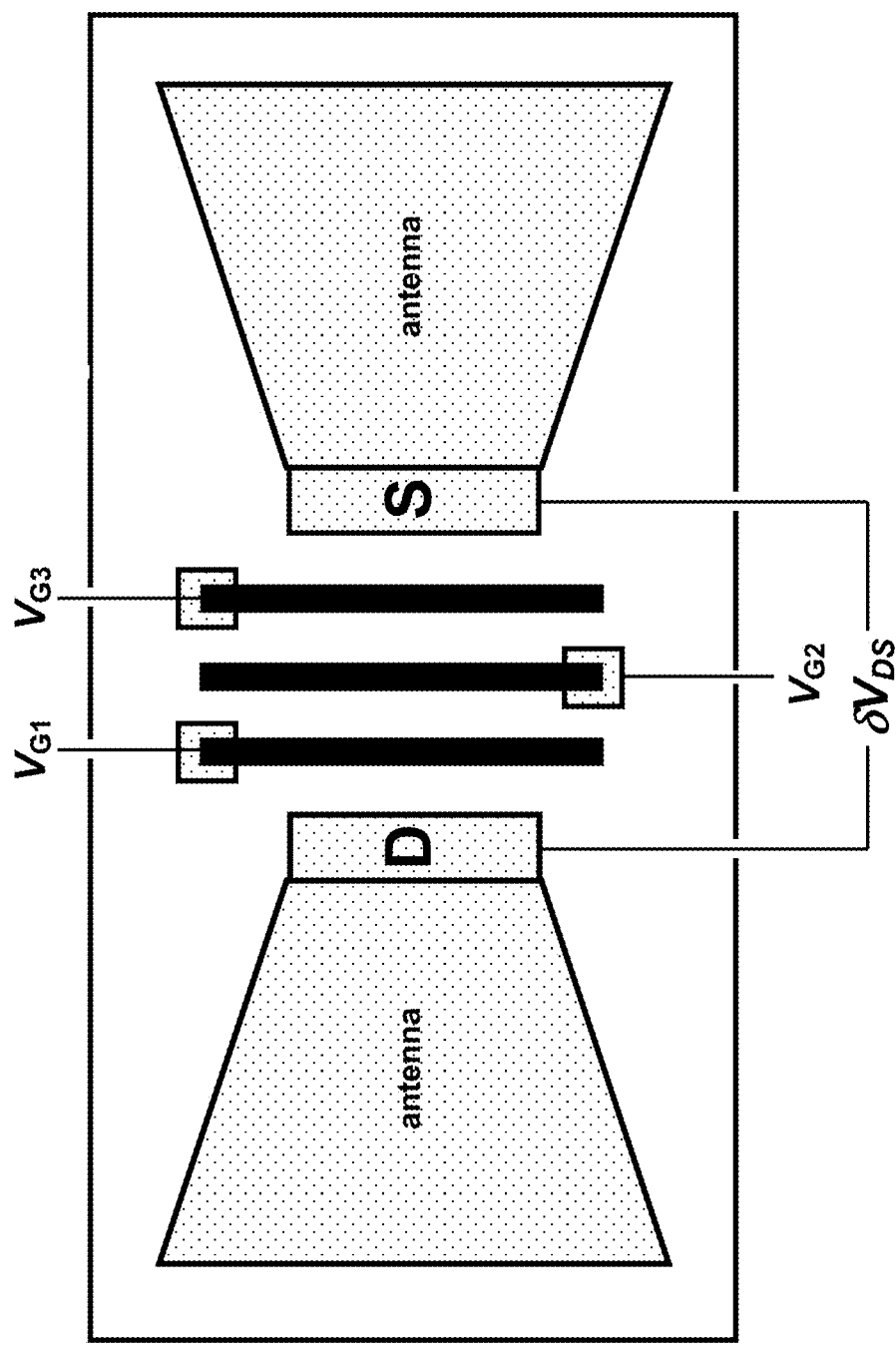
FIG. 2(b) is a top-view schematic illustration of the plasmonic interferometer further comprising an antenna for coupling incident radiation in the 2DEG layer.

In FIG. 2(b) is shown a schematic top-view illustration of the plasmonic interferometer. An antenna optimized for a particular band can couple the incident electromagnetic radiation to the interferometer at the antenna vertex in a quasi-optical configuration. The incident field is coupled to the source and drain terminals of the HEMT, while the gate biases $V_{G1}$, $V_{G2}$, and $V_{G3}$ modulate the resonant 2D plasmonic modes and the detector response. In this scheme, the THZ fields also couple capacitively to all terminals, though the antenna is directly connected to S and D. See G. C. Dyer et al., *Proc. of SPIE* 8363, 83630T (2012). Alternatively, a broadband antenna with or without a hyper-hemispherical lens can be used to improve the coupling efficiency. For example, the broadband antenna can be a log-periodic antenna with a physical diameter of order millimeters. For example, the lens can comprise a material that is transparent to the incident radiation, such as silicon. The lens can narrow the beam spot illuminating the active area of the antenna and improve impedance matching of the antenna to the medium of the incident electromagnetic field, thereby enhancing detector response.

Exemplary Plasmonic Interferometer

Figure 3A:
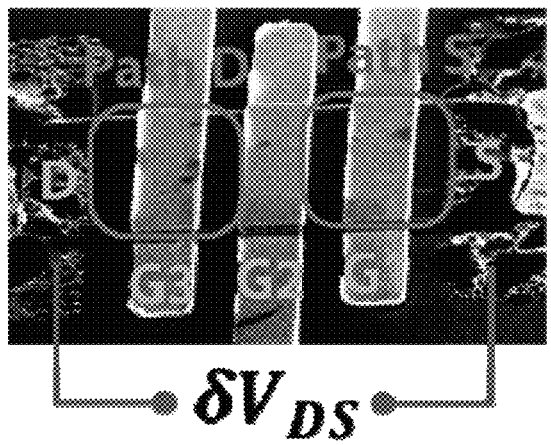
FIG. 3(a) is a top-view scanning electron micrograph (SEM) of a two-path plasmonic interferometer where gate G2 of a HEMT defines the mixing element and Path S and Path D are tuned by G1 and G3, respectively.
Figure 3B:
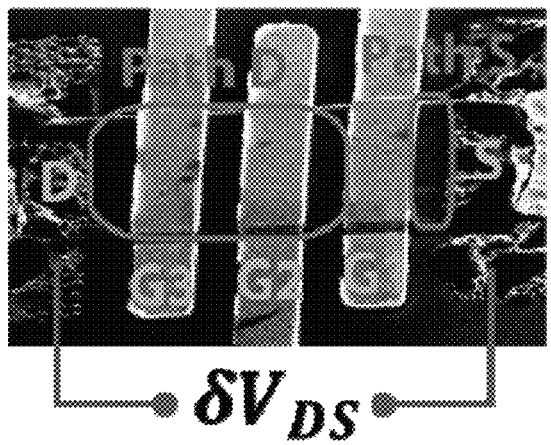
FIGS. 3(b) and 3(c) are SEMs of the same interferometer, but with G1 and G3, respectively, defining the mixing region.
Figure 3C:
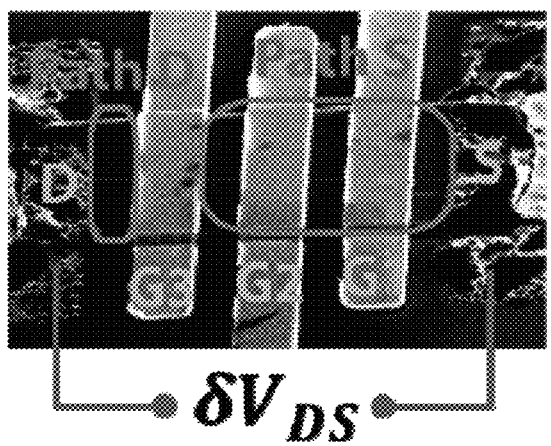

As an example of the invention, a plasmonic interferometer with an integrated resonant homodyne mixing element based upon a GaAs/AlGaAs HEMT with multiple gate terminals was fabricated. FIG. 3(a) is a scanning electron micrograph of the two-path plasmonic interferometer where gate G2 of a HEMT defines the mixing element and source-side Path S and drain-side Path D are tuned by G1 and G3, respectively. In this interferometer, the gates are all approximately 2 µm wide and separated by 2 µm. The distance between the Ohmic contacts S and D is 14 µm. FIGS. 3(b) and 3(c) show the same device but with G1 and G3, respectively, defining the mixing region.

Figure 1:
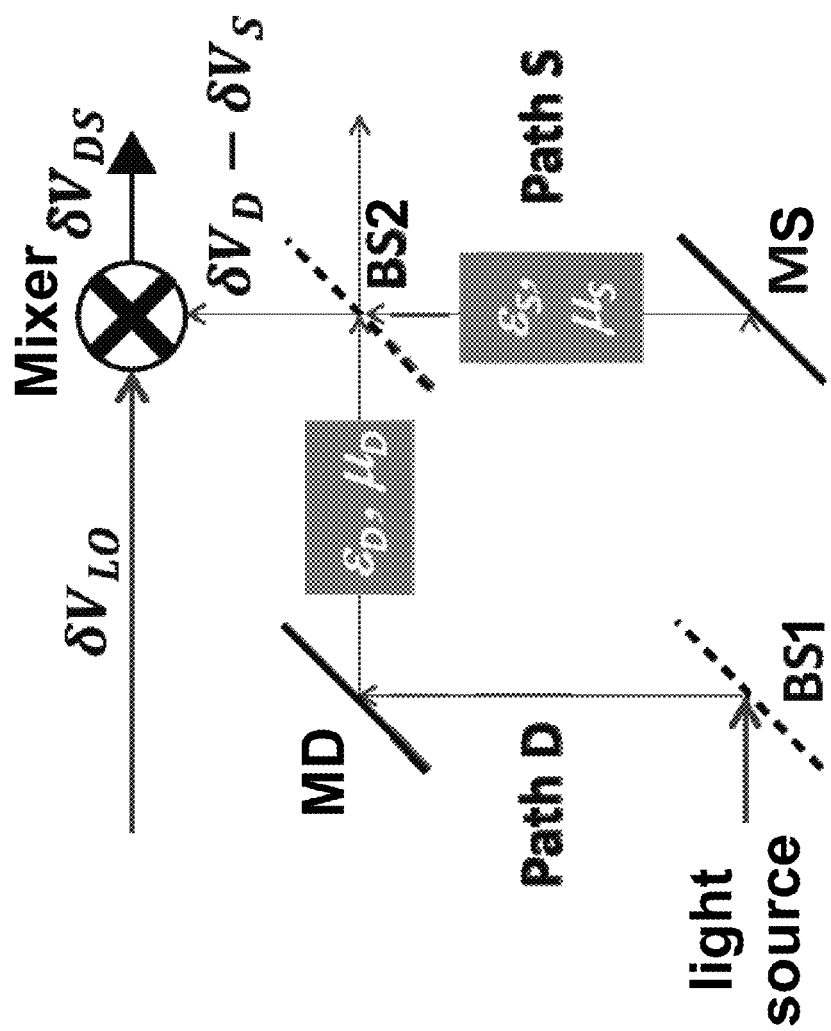
FIG. 1 is a diagram of the layout of an optical Mach-Zehnder interferometer where the electromagnetic properties of Path D and Path S are independently defined.
Figure 4:
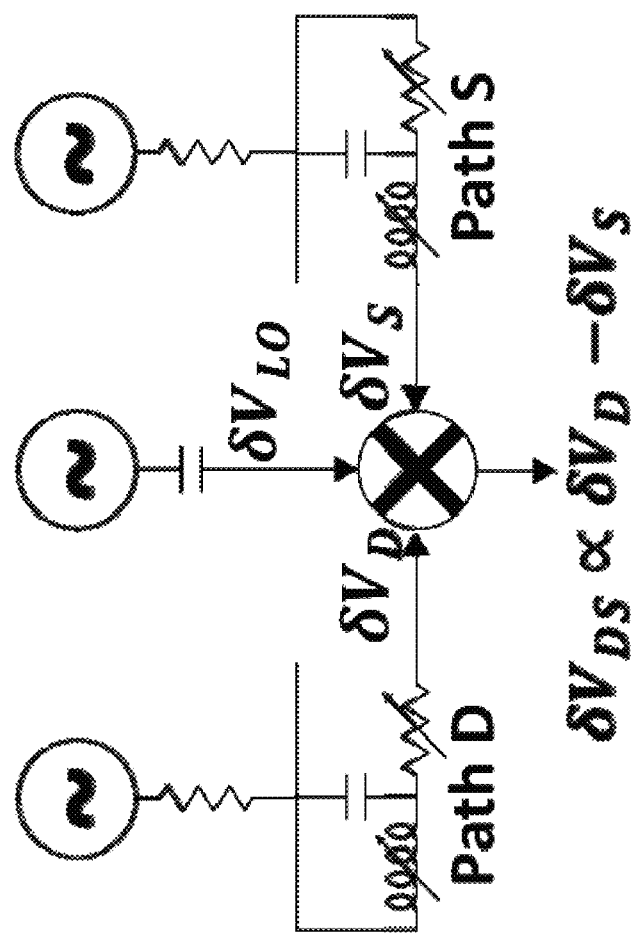
FIG. 4 is an equivalent circuit schematic for a two-path plasmonic interferometer where Path D and Path S are independently tunable.

FIG. 4 shows a transmission line circuit of the plasmonic interferometer in FIGS. 2 and 3, representing a pair of 2D plasmonic cavities coupled to a plasmonic mixing element. While the equivalent circuit describes the invention as-realized in a HEMT, it also generally depicts a plasmonic interferometer where, for example, the mixing element could be a discrete component coupled with 2D plasmonic waveguides. This representation of a 2D plasmonic HEMT is analogous to the optical Mach-Zehnder interferometer in FIG. 1 provided that the plasmonic cavities in Path S and Path D are driven in phase with equal amplitude and the variable inductances and resistances in each cavity are independently tunable. A local oscillator (LO) field is coupled to the mixer to produce a down converted, or rectified, direct current (DC) signal by mixing with the fields incident from Path D and Path S. This homodyne mixing response containing two signal paths that are effectively 180 degrees out-of-phase can be understood through analyzing the non-linear response of a plasmonic HEMT as follows.

Resonant Plasmonic Homodyne Mixing in HEMTs

A resonant plasmonic photoresponse in the HEMT as shown in FIGS. 2 and 3 under THz illumination may arise from several mechanisms. Recent studies have revealed a bolometric THz response mechanism, while a photovoltage may also result from THz excitation when the 2DEG is at or near depletion. See V. M. Muravev and I. V. Kukushkin, *Appl. Phys. Lett.* 100, 082102 (2012); G. C. Dyer et al., *Appl. Phys. Lett.* 97, 193507 (2010); G. C. Dyer et al., *Appl. Phys. Lett.* 100, 083506 (2012); G. C. Dyer et al., *Phys. Rev. Lett.* 109, 126803 (2012); and G. C. Dyer et al., *Nature Photon.* 7, 925 (2013). The analysis below assumes the latter mechanism, a resonant plasmonic homodyne mixing photoresponse.

The time-averaged mixing signal under THz illumination can be described in terms of the in-plane plasmonic voltages coupled to a region of 2DEG, $$\langle \partial V_{DS} \rangle = -G_{DS} \frac{\partial R_{DS}}{\partial V_{Gj}} \langle \partial V_{LO}(t)[\partial V_D(t) - \partial V_s(t)] \rangle. \quad (1)$$

See A. Lisauskas et al., *J. Appl. Phys.* 105, 114511 (2009); W. Knap et al., *J. Infrared, Milli., and THz Waves* 30, 1319 (2009); and S. Preu et al., *J. Appl. Phys.* 111, 024502 (2012). The conductance $G_{DS}$ and resistance $R_{DS} = 1/G_{DS}$ between drain D and source S can be found from DC transport measurements. The conductance and resistance found from two-point transport measurements includes series contributions from contacts and channel access regions in addition to a region of the HEMT channel tuned by a gate. However, when a gate is biased near its threshold voltage, the transport properties of the channel below the gate dominate over additional series contributions. In this limit, $G_{DS}$ and $R_{DS}$ can then be taken to describe the transport in the plasmonic mixing region. The time dependent voltages in Eq. (1) represent the THz fields coupled from opposing edges (contacts) to the mixing region below a gate biased near depletion. For generality, it is assumed that there can be more than one gate, with Gj denoting the $j^{th}$ gate. The LO voltage $\partial V_{LO}(t)$ is capacitively coupled from Gj to the 2DEG, while $\partial V_D(t)-\partial V_S(t)$ is the difference of the THz near fields coupled to the drain and source sides of the depleted region below gate Gj. Here $\partial V_D(t)$ and $\partial V_S(t)$ are treated as fully independent signals. Because the polarity of the net photovoltage will depend upon which side of the mixing region the 2DEG generates a larger shift in 2DEG chemical potential, these two independent rectified signals are subtracted rather than added. This produces the effective, built-in 180 degree phase offset between the two signal paths.

With G2 of a three-gate GaAs/AlGaAs HEMT tuned to deplete the 2DEG below it as illustrated in FIG. 3(a), rectification takes place both at the left edge of G2 where the signal from Path D couples to the central mixing region as well as at the right edge of G2 where the signal from Path S couples to the mixing region. Thus, the DC potential $\langle \partial V_{DS} \rangle$ arises due to the difference between the rectified voltages on the drain-side of G2 and the source-side of G2. One of the underlying assumptions in this model is a loss of coherence between the two plasmonic signal channels when the mixing region of the 2DEG between them is biased near depletion. Modeling by Davoyan and Popov indicates that as $n_{2DEG} \rightarrow 0$, the plasmon near field amplitude decays rapidly from the edges of this region into its center. See A. R. Davoyan, V. V. Popov, and S. A. Nikitov, *Phys. Rev. Lett.* 108, 127401 (2012); and A. R. Davoyan, and V. V. Popov, *Opt. Commun.* 315, 352 (2014). This isolates the plasma excitations at opposing edges from one another, and is consistent with the experimental assumption that these decoupled plasmonic fields produce independent mixing signals.

Figures 5A, 5B, 5C:
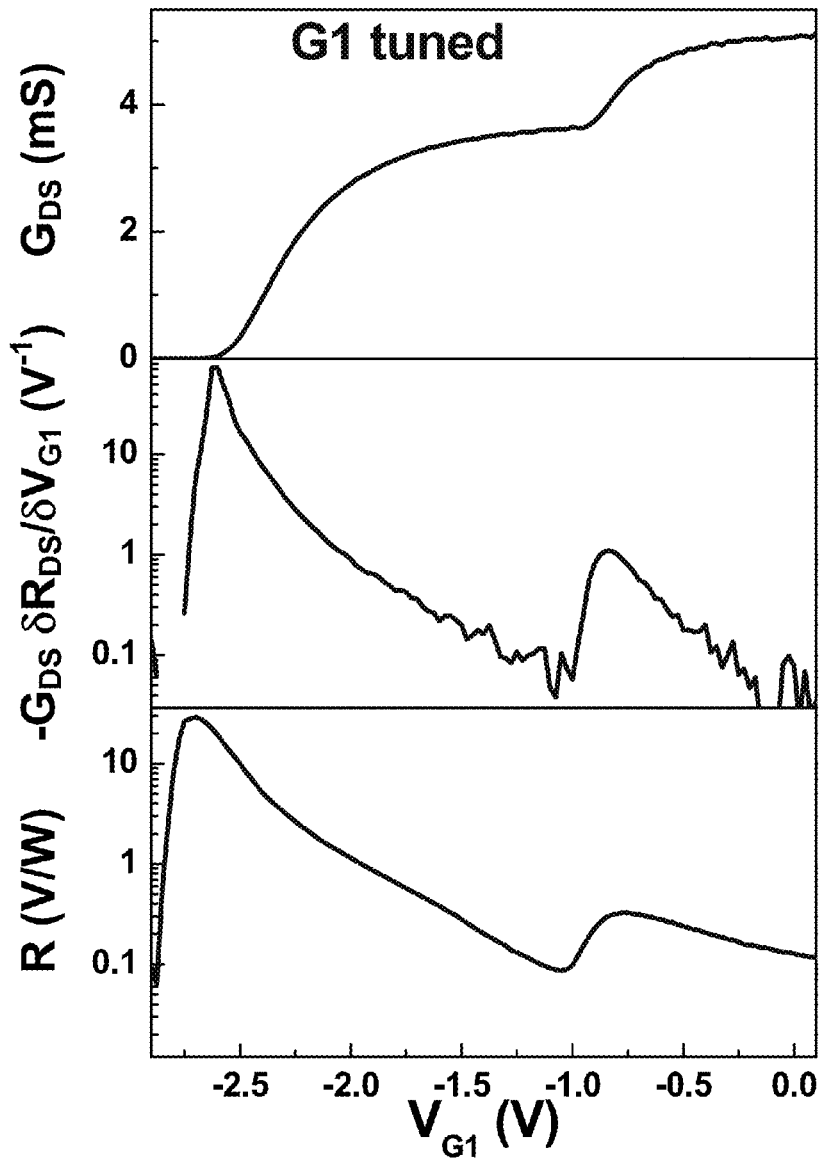
FIG. 5(a) is a plot of the channel conductance at 8 K of the HEMT illustrated in FIG. 3 plotted as a function of voltage applied to gate G1.
FIG. 5(b) is a plot of the product $$-G_{DS}\frac{\partial R_{DS}}{\partial V_{G1}},$$
FIG. 5(c) is a plot of the 8 K device photoresponse under 0.270 THz illumination as a function of voltage applied to G1.

While in FIG. 3(a) G2 defines the mixing region of the device as shown, in fact any of the gates Gj can induce a plasmonic mixing region. In FIGS. 3(b) and 3(c), alternative possibilities where G1 and G3, respectively, induce the mixing region are illustrated. The three possible choices for plasmonic mixing region of this device are explored through a combination of transport and photoresponse measurements at 8 K in FIGS. 5 and 6. Measurements of the device transport were performed using a lock-in amplifier (LIA) to source 4.0 mV at 75.0 Hz to a 5.1 kOhm load resistor in series with the sample maintained at 8 K in a cryostat. The voltage drop across the load resistor was measured using the LIA to determine the device conductance as the sample gate biases were tuned. In FIG. 5(a), the device conductance as the voltage applied to G1 of the three-gate HEMT in FIGS. 3(a)-(c) is tuned is shown. Though this two-point measurement includes contact resistances as well as series contributions from wire bonds, several key features directly related to the HEMT channel are evident. There is a discontinuity in the conductance near $V_{G1}=-0.95$ V that indicates the presence of a parallel conduction channel in the device. In fact, the GaAs/AlGaAs heterostructure in this device had two quantum wells with a combined 2D electron density of $4.0 \times 10^{11}$ cm$^{-2}$ that conducted in parallel. This discontinuity feature results from the depletion of the quantum well nearest to the gate. The full depletion of both quantum wells below G1 is evident around $V_{G1}=-2.60$ V. In this regime, transport in the region immediately below G1 dominates the system and contact resistances are negligible in comparison.

The DC measurement of the device conductance is connected with the expected THz photoresponse through Eq. 1. The factor $$-G_{DS}\frac{\partial R_{DS}}{\partial V_{Gj}}$$

in Eq. 1 relates the DC transport of a HEMT to its plasmonic mixing response, and is plotted in FIG. 5(b) as calculated from the conductance in FIG. 5(a). To verify that Eq. 1 and its corresponding transport measurement in FIG. 5(b) accurately describe the plasmonic mixing response, the photoresponse plotted in FIG. 5(c) was measured at 8 K with a 0.270 THz signal quasi-optically steered and focused on the device at normal incidence to the GaAs substrate. The external responsivity was calculated using the THz power incident on the window of the cryostat to normalize the measured voltage signal. Because this definition of the responsivity neglects window losses as well as power focused outside of the active area of the antenna, it should be understood as lower bound estimate of the detector responsivity.

A broadband THz antenna and a Si lens was used to improve the coupling efficiency. See G. C. Dyer et al., *Proc. of SPIE* 8363, 83630T (2012). The incident THz radiation was linearly polarized orthogonal to the HEMT channel between S and D contacts in order to match the co-polarization axis of the antenna. While this polarization weakly excites plasmons along the HEMT channel in the absence of an antenna, for the chosen antenna layout this polarization provides optimal plasmonic coupling to the incident THz field.

A LIA modulated a continuous wave Schottky diode multiplier millimeter wave source (Virginia Diodes, Inc.) at 196.7 Hz and also measured the photovoltage generated between the source and drain terminals of the device under 0.270 THz illumination. Interestingly, circuit loading effects due to the HEMT RC time constant under typical bias conditions can become significant around several kHz modulation and reduce the measured photoresponse. See M. Sakowicz et al., *J. Appl. Phys.* 110, 054512 (2011). Thus the conventional circuit RC limited bandwidth is on the order of kHz, yet underdamped plasma excitations nonetheless provide coupling of THz fields to a high-resistance mixing region.

Through comparison of FIGS. 5(b) and (c), it is evident that the measured photovoltage correlates strongly with the calculated transport curve, $$-G_{DS}\frac{\partial R_{DS}}{\partial V_{G1}}.$$

Both data sets have maxima where the upper and lower quantum well channels below G1 are depleted, and also demonstrate an approximately three order of magnitude dynamic range. Although the plasmonic mixing response shown in FIG. 5 is largely unsurprising given the many demonstrations of this mechanism in highly varied transistor designs, material systems, and temperature ranges, definitively establishing the origin of this photoresponse provides the basis for describing the operation of a two-path plasmonic interferometer. See D. Coquillat et al., *Opt. Express* 18, 6024 (2010); S. Preu et al., *IEEE Trans. on THz Sci. and Tech.* 2, 278 (2012);

W. Knap et al., *Appl. Phys. Lett.* 81, 4637 (2002); W. Knap et al., *J. Infrared, Milli., and THz Waves* 30, 1319 (2009). F. Teppe et al., *Appl. Phys. Lett.* 87, 052107 (2005); A. El Fatimy et al., *Appl. Phys. Lett.* 89, 131926 (2006); A. Shchepetov et al., *Appl. Phys. Lett.* 92 (2008); V. V. Popov et al., *Appl. Phys. Lett.* 98, 153504 (2011); P. Földesy, *Opt. Lett.* 38, 2804 (2013); P. Földesy, *J. Appl. Phys.* 114, 114501 (2013). Asymmetry in the plasmonic signals coupled to the mixing region, $\partial V_D(t) - \partial V_S(t) \neq 0$, is required for generating a non-zero photovoltage. See V. V. Popov et al., *Appl. Phys. Lett.* 99, 243504 (2011); and T. Watanabe et al., *Solid-State Electronics* 78, 109 (2012). One means to explore introducing asymmetry into the device is by systematically voltage biasing each of the three gates.

Figures 6A, 6B:
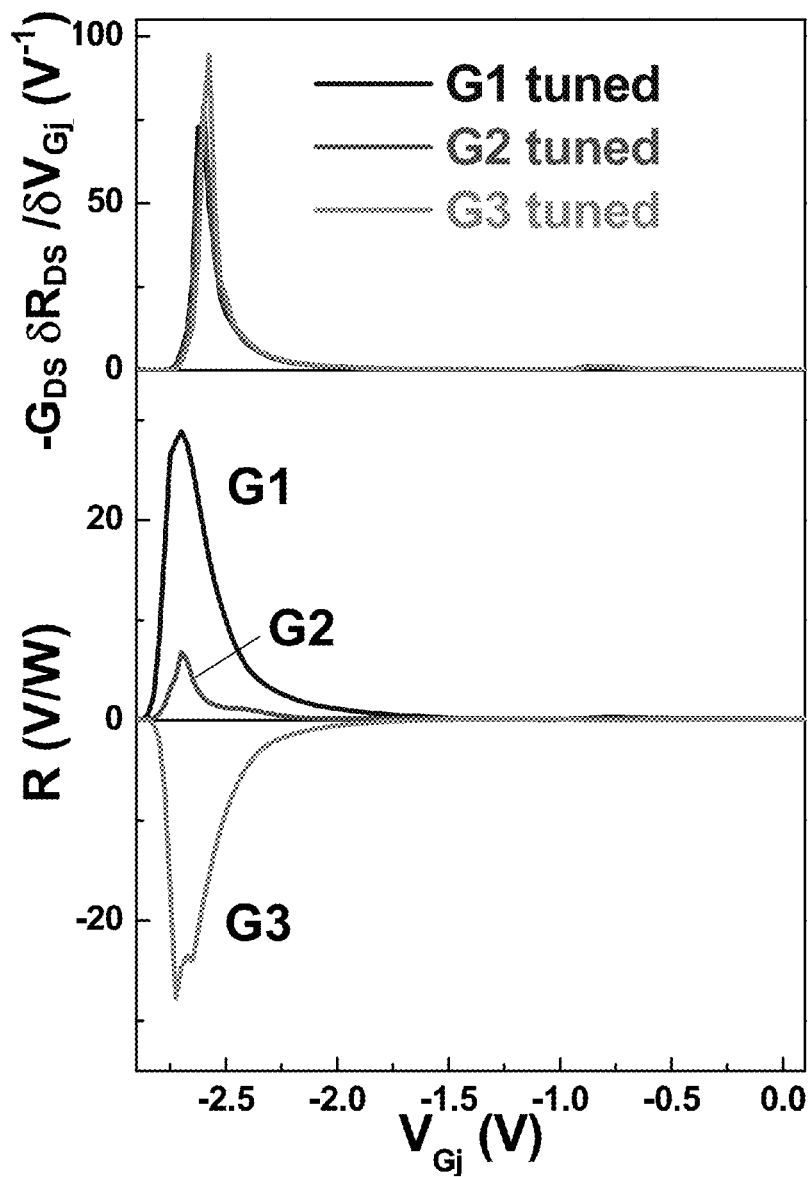
FIG. 6(a) is a plot of the product $$-G_{DS}\frac{\partial R_{DS}}{\partial V_{Gj}}$$
FIG. 6(b) is a plot of the 8 K device photoresponse under 0.270 THz illumination as a function of voltage applied to gates G1, G2, and G3.

In FIG. 6, the transport and responsivity characteristics at 8 K of the HEMT are compared as one of the three gates is tuned independently while the other two are fixed at ground potential. The transport curves corresponding to Eq. 1 that are plotted in FIG. 6(a) are all nearly identical, consistent with the HEMT channel being homogeneous across the device and all three gates sharing an identical 2 μm width. Thus, the differences in the 0.270 THz responsivity shown in FIG. 6(b) arise due to asymmetry in the device induced via the applied gate bias. The responsivity with either gate G1 or gate G3, respectively, tuned is nearly identical in amplitude, but opposite in polarity. Taking G1 to define the mixing region as illustrated in FIG. 3(b), there are two plasmonic paths feeding into this mixing region: a path formed between S and G1 and a path formed between D and G1. Because these paths are different lengths, 2 μm vs. 10 μm, the phase and amplitude of monochromatic plasma waves impinging on the mixing region below G1 from opposing sides will, in general, be non-identical. This produces a net photoresponse because $\partial V_D(t) - \partial V_S(t) \neq 0$. The scenario is similar when G3 defines the mixing region as shown in FIG. 3(c), but now the short and long plasmonic paths have exchanged relative positions in comparison to the first example. Consistent with the measured data, this inverts the signal polarity but leaves its amplitude largely unaffected.

A third possibility, pictured in FIG. 3(a), utilizes gate G2 to define the mixing region. In this case, the device is essentially symmetric about gate G2, though fabrication imperfections or misalignment of the incident radiation can introduce asymmetries. Here the photoresponse should be relatively weaker since the phase and amplitude of monochromatic plasma waves impinging on the mixing region from both paths will be nearly identical such that $\partial V_D(t) - \partial V_S(t) \approx 0$. In FIG. 6(b) the photoresponse with G2 tuned has a smaller amplitude, though its measureable amplitude indicates some asymmetry in the system under THz irradiation. Nonetheless, this is the most near-to-balanced configuration and also offers independent tunability of both Path D and Path S. Using this configuration, the operation of a monolithically integrated, balanced two-path plasmonic interferometer is described below.

Two-Path Plasmonic Interferograms

With G2 biased to deplete the 2DEG below it, the plasmonic paths between S and G2 (Path S) and D and G2 (Path D) can be described in terms of tunable electrical lengths. Each of these paths is 6 μm long, with 2 μm regions below gates G1 and G3 that can be voltage tuned. It is these sections below gates G1 and G3 that are of greatest interest, and it is useful to first relate applied gate voltages to 2DEG densities. Assuming a parallel plate capacitance between each gate and the 2DEG, $$n_{1,3} = n_0 \frac{V_{th} - V_{G1,G3}}{V_{th}}, \quad (2)$$

where $n_0$ is the intrinsic 2DEG density of $4.0 \times 10^{11}$ cm$^{-2}$ and $V_{th}$ is the threshold voltage where the 2DEG is depleted, $V_{th} \cong -2.60$V. Since the equivalent distributed circuit elements in FIG. 3(a) depend directly upon $n_{1,3}$, the complex-valued transmission line propagation constants for Path S and Path D, $$q_{S,D} = -i\sqrt{i\omega C_{1,3}(i\omega L_{1,3} + R_{1,3})}, \quad (3)$$

can be defined for the voltage-tuned regions below G1 and G3, respectively. Here the distributed kinetic inductance $L_{1,3} = m^*/e^2 n_{1,3}$, distributed resistance $R_{1,3} = L_{1,3}/\tau$ and distributed 2DEG capacitance $C_{1,3} = \epsilon q_{S,D}(1 \coth q_{S,D} d)$ where $m^*$ is the electron effective mass of $0.067 m_e$, e is the electron charge, τ is the plasmon damping time, ε is the permittivity of GaAs, and d is the separation between the gates and the 2DEG. See G. R. Aizin and G. C. Dyer, *Phys. Rev. B* 86, 235316 (2012). The inductance and resistance follow from the Drude model. Because the plasmonic fields surrounding the 2DEG generally have a longitudinal electric field component, the capacitance depends upon q as well as d. However, in the long wavelength limit ($q_{S,D} d \ll 1$) where the gate screens the plasmon, $C_{1,3} = \epsilon/d$, a parallel plate capacitance. In general, Eq. 3 is a transcendental equation, though it is identical to the standard definition of the propagation constant in transmission line theory as written in terms of equivalent circuit parameters. Though the total electrical lengths of Path S and Path D will also include the 4 μm of untuned 2DEG, it is sufficient to consider only the tuned regions to find the difference in electrical lengths. Thus, the relevant electrical lengths for Paths S and D are, $$\theta_{S,D} = a q'_{S,D}, \quad (4)$$

where $q_{S,D} = q'_{S,D} + i q''_{S,D}$, $q'_{S,D}$ and $q''_{S,D}$ are real, and a=2 μm. Then the difference in electrical lengths of the two paths is $\Delta\theta_{S,D} = a(q'_D - q'_S)$. Physically, as either G1 or G3 is tuned towards threshold voltage, the electron density is decreased, the 2DEG (kinetic) inductance increases, the plasmon wavelength decreases, and the propagation constant increases.

The interferometric plasmonic signal with Path S and Path D independently controlled is illustrated in FIGS. 7(a) and (b). These experimental measurements were performed at 8 K for excitation frequencies of 0.270 and 0.360 THz, respectively, with $V_{G2} = -2.55$V. Because the gate voltage, the 2DEG density, the plasmon propagation constant, and the electrical length are all directly related by Eqs. 2-4, any of these may effectively parameterize the tuning of Paths S and D. In FIG. 7, the electrical lengths $\theta_{S,D}$ corresponding to Path S and Path D are used in plotting the plasmonic interferogram. The diagonal lines from the lower left to upper right corners of FIGS. 7(a) and (b) indicate where $\Delta\theta = 0$. This can be viewed as a 180 degree phase shift between the two identical paths when otherwise excited identically. For the balanced two-path interferometer, this diagonal marks where the signal should vanish as well as the boundary about which the signal should have anti-mirror symmetry. This is equivalent to stating that the signal $S(\theta_S, \theta_D)$ obeys the relation $S(\theta_1, \theta_2) = -S(\theta_2, \theta_1)$. Though the experimental results plotted in FIGS. 7(a) and (b) do not precisely follow this rule as would be the case in ideal balancing of the two paths, the qualitative picture nonetheless is indicate of anti-mirror symmetry. The signal tends to weaken then change polarity along $\Delta\theta = 0$ and for each positive signal polarity resonance at a coordinate ($\theta_1,\theta_2$) there tends to be a companion resonance at $\theta_2,\theta_1$) with negative polarity.

Figures 7C, 7D:
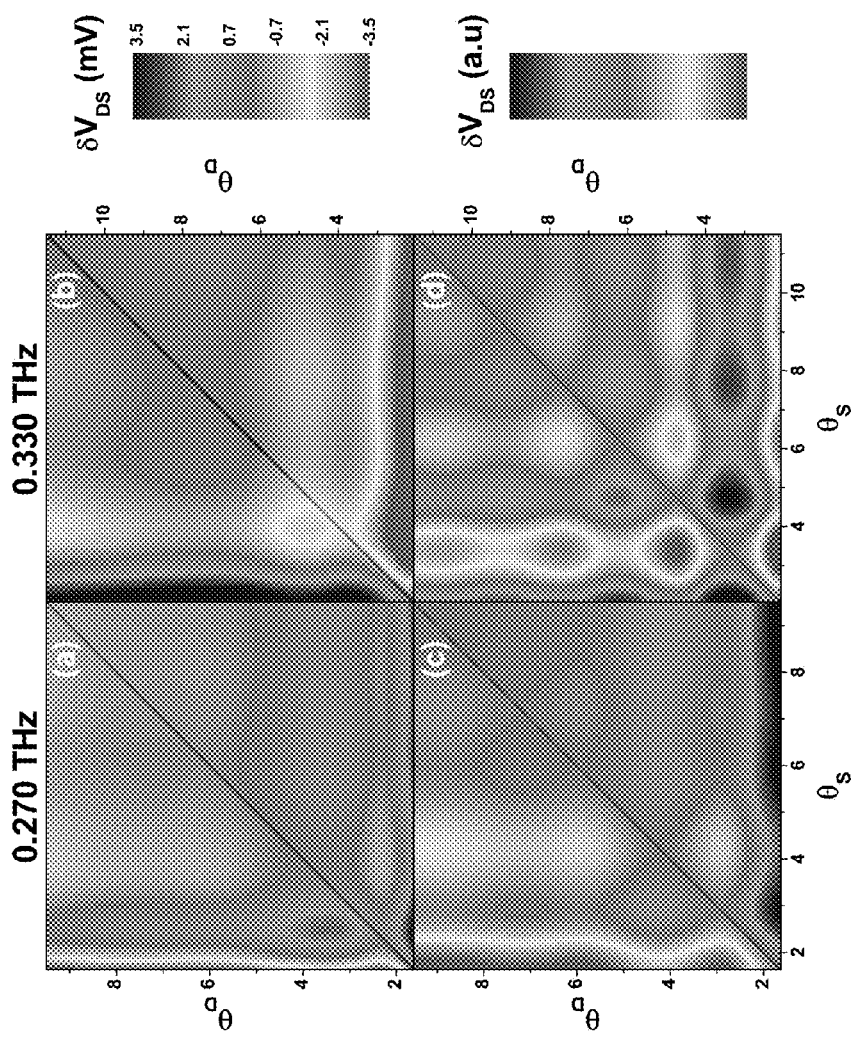
FIGS. 7(c) and 7(d) show model calculations of the photoresponse under 0.270 THz and 0.330 THz excitation, respectively, plotted using a transmission line formalism to describe the independent signals from Paths S and D coupled to the mixing element below G2.

The quantity Re[$\partial V_D$–$\partial V_S$] calculated using a plasmonic transmission line model as shown in FIG. 4 is plotted in FIGS. 7(c) and (d) for excitation frequencies of 0.270 and 0.360 THz using the plasmonic transmission line model. Here it is assumed the antenna functions as a lumped element voltage source with an internal impedance found from its radiation resistance. See G. C. Dyer et al., *Phys. Rev. Lett.* 109, 126803 (2012). Additionally, because the equivalent circuit sources driving the LO, Path S and Path D are in-phase, the real parts of the calculated plasmonic transmission line voltages can be calculated to emulate the anticipated plasmonic mixing response. There is very good agreement between experimental and model interferograms in FIGS. 7(a) and (c) using this approach, with several resonances matched in polarity observable along both the vertical and horizontal axes. However, the model interferogram in FIG. 7(d) does not match the experimental interferogram in FIG. 7(b) as well. Although the lower order resonances seen at the shortest electrical lengths have the same polarity in FIGS. 7(b) and (d), the model calculations predict additional higher order resonances that are not observed experimentally. Part of the discrepancy may arise from higher experimental plasmonic damping rates than the damping rate corresponding to an electron mobility of 100,000 cm$^{-2}$/V-s used in the model calculations. As the electrical length is increased by gate tuning, the losses increase, the resonances broaden, and the signal amplitude decreases. This is a qualitative feature of all plots in FIG. 7, and it is possible that the higher order modes in FIG. 7(d) cannot be resolved.

Figures 8A, 8B:
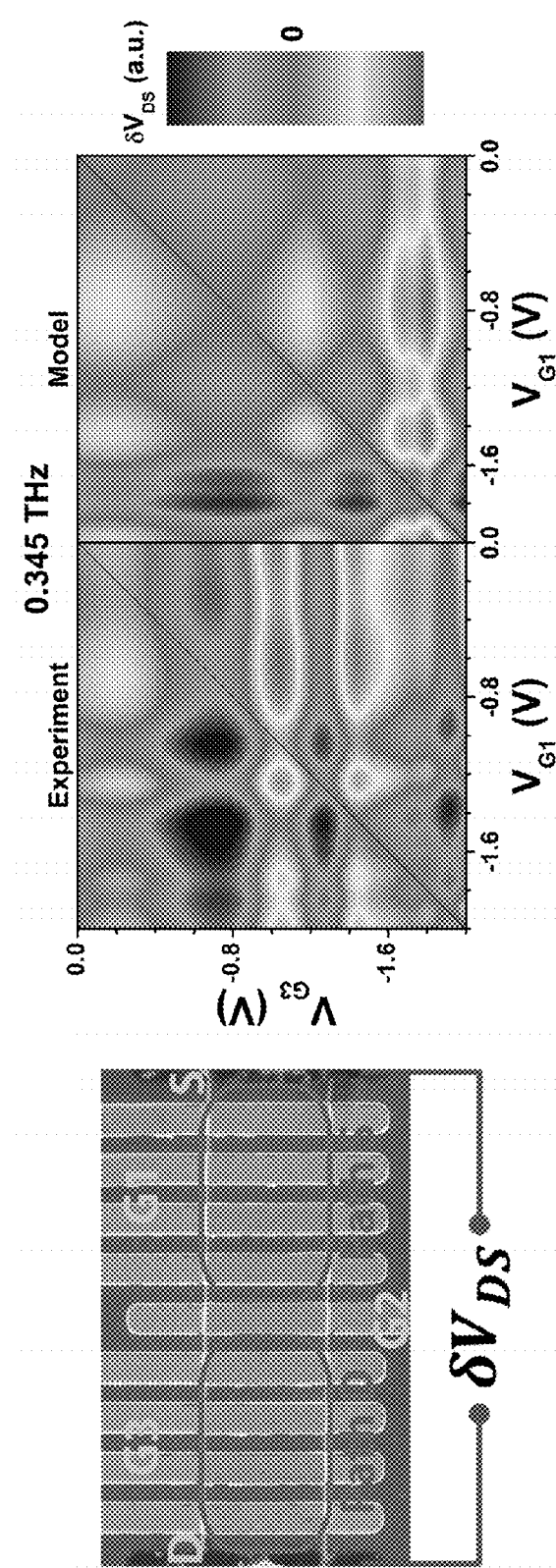
FIG. 8(a) is a scanning electron micrograph of a two-path plasmonic crystal interferometer where gate G2 of the HEMT defines the mixing element and Path S and Path D are tuned by G1 and G3, respectively.
FIG. 8(b) is a plot of the 8 K device photoresponse under 0.345 THz illumination, mapped as a function of voltage applied to gates G1 and G3 with G2 fixed at −2.80 V in the left frame. A model calculation of the photoresponse under 0.345 THz illumination is also plotted in the right frame using a transmission line formalism to describe the independent signals from Paths S and D coupled to the mixing element below G2.

To further demonstrate the invention, a second exemplary device design, shown in FIG. 8(a), was considered where the two plasmonic paths are independently tunable four-period plasmonic crystals. See G. C. Dyer et al., *Nature Photon.* 7, 925 (2013). Here G2 is a single 2 μm gate, and G1 and G3 tune Path S and Path D, respectively, using four identically tuned 2 μm wide gate stripes separated by 2 μm each. The distance between the Ohmic contacts S and D is 34 μm. In this device, the gate tuning of plasma wave propagation cannot be interpreted as a simple change of electrical length. Because plasmons are Bragg scattered in this short periodic lattice, a crystal quasi-momentum defined by the Bloch wavevector better describes plasma wave dispersion than the propagation constant of a plasmon below G1 or G3. The experimentally measured plasmonic interferogram in the left frame of FIG. 8(b) with 0.345 THz excitation and G2 biased to $V_{G2}$=−2.80 V at 8 K is therefore plotted in terms of gate voltages $V_{G1}$ and $V_{G3}$. This plasmonic interferometer can be understood as an in-situ plasmonic spectrometer for a more complicated plasmonic heterostructure than the device shown in FIGS. 3(a)-(c). As before, plasmonic homodyne mixing takes place at the left and right edges of G2, but multi-period structures between S and G2 and D and G2 control the signals coupled to this mixing region. Despite the additional complexity of Paths S and D, a striking anti-mirror symmetry about $V_{G1}$=$V_{G3}$ where $S(V_1,V_2)$=−$S(V_2,V_1)$ is observed, indicating a well-balanced two-path plasmonic system.

A model interferogram of the calculated quantity Re[$\partial V_D$– $\partial V_S$] is plotted in the right frame of FIG. 8(b) for an excitation frequency of 0.345 THz using a plasmonic transmission line model to describe the four-period plasmonic crystals in Path S and Path D. Here a 2DEG density of 4.5×10$^{11}$ cm$^{-2}$, about 10% larger than the 2DEG density determined from Hall measurements, and an electron mobility of 600,000 cm$^{-2}$/V-s, consistent with the mobility found from Hall measurements, were used in the model calculation. Although the overall agreement with experiment is largely qualitative in nature, the expected anti-mirror symmetry about $V_{G1}$=$V_{G3}$ where $S(V_1,V_2)$=−$S(V_2,V_1)$ is present. The most significant discrepancies between the model and experiment in FIG. 8(b) likely arise as a result of approximating the THz excitation as a lumped source in the transmission line model rather than a more realistic distributed excitation. While the transmission line approach predicts the resonant modes of the system with adequate fidelity, the exact plasmonic field amplitudes of Path S and D at the edges adjacent to the mixer will depend non-trivially upon the THz excitation of each plasmonic crystal. The THz coupling impacts not only the amplitudes of resonances, but also linewidths since radiative damping is a significant broadening mechanism. Moreover, radiative damping rates will generally not be identical for all modes in the system. A lumped excitation is a reasonable approximation for plasmonic cavities with only several plasmonic elements, but limits the validity of the transmission line approach for modeling the plasmonic near fields of more complicated devices.

Several additional features in FIG. 8(b) prompt further consideration. First, in comparison to FIG. 7, many additional modes are observed with only a slight increase in excitation frequency. This is understood in part by comparing the 6 μm plasmonic path lengths in the device shown in FIG. 3(a) to the 18 μm path lengths in device shown in FIG. 8(a). The fundamental mode of the 18 μm path occurs at a lower frequency than that of the 6 μm path, and therefore a relatively denser set of higher order modes is anticipated for a given excitation frequency. Alternately, the coupling of four gated regions of the 2DEG in the device shown in FIG. 8(a) lifts a four-fold degeneracy, and therefore approximately four modes are expected for every one observed in the device of FIG. 3(a). Additionally, the highest intensity signal is observed with significant tuning of gate voltage. This would be analogous to observing the largest signal in FIG. 7 at any electrical length but the smallest measured. One possibility consistent with a recent study of localized modes in terahertz plasmonic crystals is that specific modes in the spectrum couple less well to the mixing region due to their confinement adjacent to an Ohmic contact, either source S or drain D. See G. C. Dyer et al., *Nature Photon.* 7, 925 (2013). Although the distributed nature of the THz excitation precludes validation of this hypothesis using a lumped source to model the plasmonic near field amplitude, the non-monotonic behavior of signal intensities is suggestive of the localization of plasmon modes in Path S and Path D.

Figure 9A:
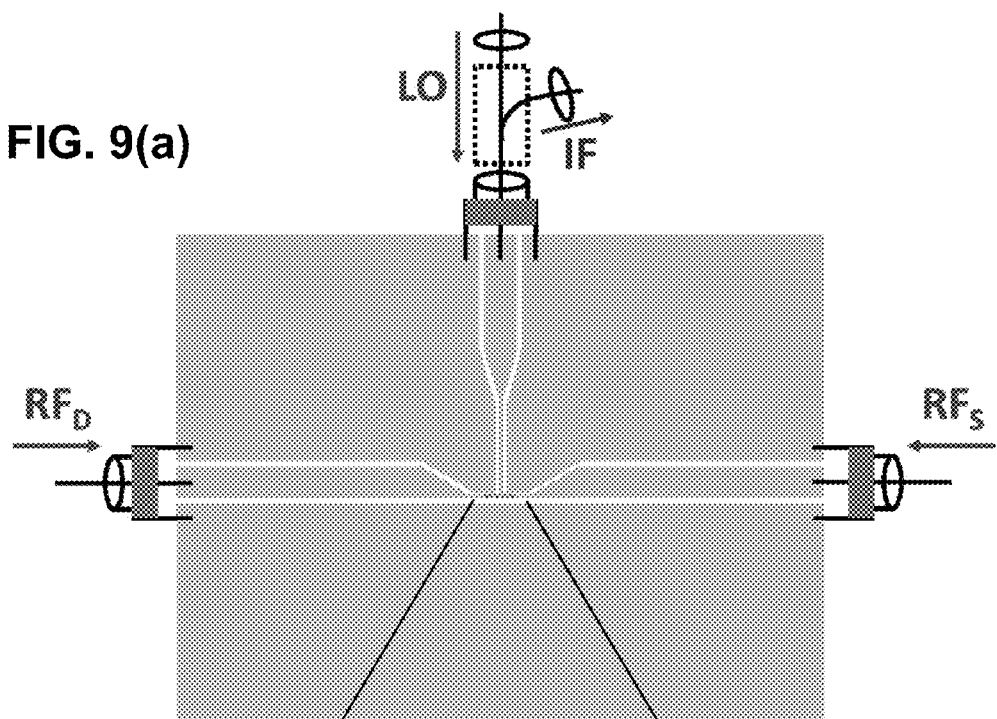
FIG. 9(a) is a schematic layout of a coplanar waveguide-based plasmonic interferometer device. Three ports with a ground-signal-ground configuration allow for coupling of signals $RF_D$ and $RF_S$ and a local oscillator LO to the plasmonic interferometer (dashed outline region). A directional coupler can be used to route the resulting intermediate frequency signal (IF) to a spectrum analyzer.
Figure 9B:
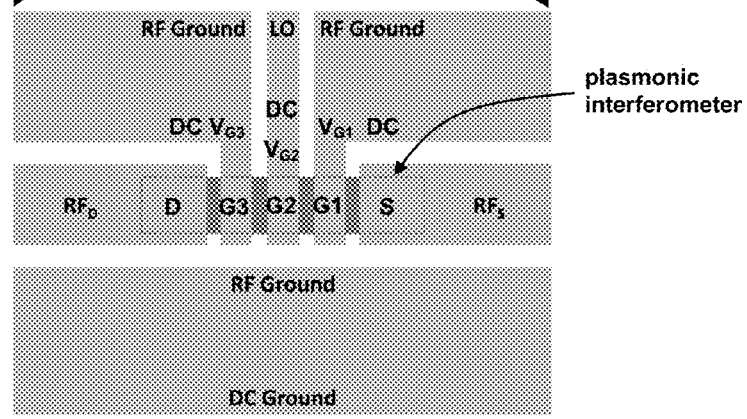
FIG. 9(b) shows detail of the plasmonic interferometer device and the DC and RF biases.

As described above, on-chip plasmonic interferometry can be integrated with a widely-used plasmonic detection technique. Although the exemplary devices used an antenna to provide the distributed excitation of the signal channels and the LO of the plasmonic mixer, waveguide-coupled structures can also be used if the LO and signal channels are suitably isolated, as illustrated in FIG. 9. See W. F. Andress et al., *Nano Lett.* 12, 2272 (2012); and K. Y. M. Yeung et al., *Appl. Phys. Lett.* 102, 021104 (2013), which are incorporated herein by reference. The phase relationship between the LO and signal channels is determined by the coupling of the THz excitation to HEMT terminals. Isolation of these channels allows for control of their relative phase and potentially a quadrature measurement to extract both the amplitude and phase of an incident THz signal. This possibility arises because the plasmonic mixer is a field rather than power detector. While intensity interferograms are often measured by bringing two paths coincident upon a power detector, here field phase information is partially preserved by independently generating a DC signal from each path and reading out to a single differential channel. Prior interferometric sensors have focused on optical techniques. As with the optical Mach-Zehnder interferometer, the sensitivity of 2D plasma excitations to their environment can provide a sensor wherein a phase shift is sensitive to a sample in one of the plasmonic paths. Therefore, the plasmonic interferometer of the present invention enables an electro-optical approach to near-field plasmonic sensing. Further, although the above described examples based on GaAs/AlGaAs heterostructures require both cryogenic cooling and a vacuum environment, other plasmonic materials such as graphene have neither as a requirement. The electromagnetic screening of 2D plasma waves by a metal terminal is a limiting case of environment modifying plasmon dispersion. However, more subtle effects, particularly in graphene, can arise due to plasmon-phonon coupling with an adjacent material or the coupling of plasmons with an adsorbed polymer. See Z. Fei et al., *Nano Letters* 11, 4701 (2011); H. Yan et al., *Nature Photon.* 7, 394 (2013); and Y. Li et al., *Nano Letters* (2014). The plasmonic interferometer of the present invention enables an electro-optical approach to near-field plasmonic sensing.

Integration of interferometric elements into a voltage-tunable microelectronic plasmonic device provides potential advantages over existing spectroscopic techniques, particularly in the far infrared. Though the substantial reduction in optical path length is beneficial, the most significant advantage is provided by the broad voltage tunability. The invention described above utilized an intrinsic mixing mechanism to exploit the plasmonic near-field enhancement. However, as illustrated in FIG. 4, the integration of a discrete mixing component with plasmonic elements is also viable. See U.S. Pat. No. 8,274,058 to Wanke et al., which is incorporated herein by reference. Provided the integrated mixer directly couples to the near field of plasma excitations, conventional diode-based detection elements can be used. The specific choice of technology depends upon the compatibility of material systems and process technologies. This enables, for example, frequency agile heterodyne mixers that do not rely on front-end optics for spectrally selective signal input.

Heterodyning consists of mixing a received RF signal with a LO signal. The LO signal has a frequency that is detuned from the frequency of the received RF signal. The mixer produces an output signal having an intermediate frequency IF that is equal to the difference between the frequencies of the LO and RF signals. The IF signal is tunable through the LO frequency and can be post-amplified and processed using conventional microwave techniques. Further, the LO can have a fixed output power that is generally much greater than the power of the received RF signal, thereby producing an IF output power that is proportional to the product of the powers of the LO and received RF signals.

The waveguide-coupled structure shown in FIG. 9 enables heterodyne mixing whereby two different LO and RF frequencies can generate an intermediate frequency. In this example, the incident electromagnetic radiation $RF_S$ and $RF_D$ is applied to the source S and drain D sides of the plasmonic interferometer via opposing source-side and drain-side waveguides fabricated on the chip. Voltages can be applies to gates G1 and G2 to provide source-side and drain-side plasmonic paths in the 2DEG of the interferometer. The central gate G2 can be biased to near depletion to provide a plasmonic mixer in the 2DEG region under the central gate. An LO signal having a frequency that is detuned from the frequency of the $RF_S$ and $RF_D$ signals can be applied to the plasmonic mixer via a central waveguide. The IF signal can be removed through the central waveguide and a directional coupler can be used to route the IF signal to a post processor, for example, a spectrum analyzer.

The present invention has been described as a two-path plasmonic interferometer with integrated detector. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A two-path plasmonic interferometer, comprising:
    a layer providing a two-dimensional electron gas (2DEG) or two-dimensional hole gas (2DHG);
    a source and a drain at opposing ends of the 2DEG or 2DHG layer;
    a source-side gate, a central gate, and a drain-side gate disposed on and separated from the 2DEG or 2DHG layer; and
    a voltage source for applying a voltage independently to each of the gates to spatially modulate the electron or hole density in the 2DEG or 2DHG layer under each gate, thereby providing a source-side plasmonic path under the source-side gate and a drain-side plasmonic path under the drain-side gate and a plasmonic mixer under the central gate when the central gate is biased to near depletion;
    wherein a standing plasma wave from the source-side plasmonic path couples with a standing plasma wave from the drain-side plasmonic path interfere at the plasmonic mixer to provide a photoresponse when incident electromagnetic radiation is coupled to the 2DEG or 2DHG layer.

2. The two-path plasmonic interferometer of claim 1, wherein the incident electromagnetic radiation has a frequency of between 10 GHz and 60 THz.

3. The two-path plasmonic interferometer of claim 1, wherein the source-side gate, central gate, and drain-side gate each comprise one or more finger electrodes.

4. The two-path plasmonic interferometer of claim 1, wherein the length of the source-side and drain-side plasmonic paths are each less than $\frac{1}{10}$ the free space wavelength of the incident electromagnetic radiation.

5. The two-path plasmonic interferometer of claim 1, wherein the source-side plasmonic path and the drain-side plasmonic path have equal plasmonic lengths.

6. The two-path plasmonic interferometer of claim 1, wherein the 2DEG or 2DHG density under the central gate electrode is sufficiently depleted so that the coherence length of the plasmonic excitation is less than the length of the mixing region under the central gate.

7. The two-path plasmonic interferometer of claim 1, wherein the layer providing the 2DEG is formed at a semiconductor heterojunction formed between two semiconductor materials having different band gaps.

8. The two-path plasmonic interferometer of claim 7, wherein the heterojunction comprises a III-V heterojunction.

9. The two-path plasmonic interferometer of claim 8, wherein the III-V heterojunction comprises GaAs/AlGaAs, InGaAs/InAlAs, GaN/AlGaN, or GaSb/InAs.

10. The two-path plasmonic interferometer of claim 1, wherein the layer providing the 2DEG or 2DHG comprises an atomically thin material having high electron mobility or high hole mobility.

11. The two-path plasmonic interferometer of claim 10, wherein the atomically thin material having high electron mobility comprises graphene.

12. The two-path plasmonic interferometer of claim 1, further comprising an antenna to couple the incident electromagnetic radiation to the 2DEG or 2DHG layer.

13. The two-path plasmonic interferometer crystal of claim 1, further comprising a waveguide to couple the incident electromagnetic radiation to the 2DEG or 2DHG layer.

14. The two-path plasmonic interferometer crystal of claim 1, further comprising a hyper-hemispherical lens to couple the incident electromagnetic radiation to the 2DEG or 2DHG layer.

15. The two-path plasmonic interferometer of claim 1, wherein the photoresponse is a rectified DC voltage signal measured between the source and the drain.

16. The two-path plasmonic interferometer of claim 15, further comprising means for varying the voltage of the sources-side gate and the drain-side gate and measuring an interferogram of the rectified DC voltage signal.

17. The two-path plasmonic interferometer of claim 16, further comprising means for post-processing the interferogram to provide a frequency domain spectrum of the incident electromagnetic spectrum.

18. The two-path plasmonic interferometer of claim 1, further comprising means for applying a local oscillator signal to the plasmonic mixer that has a frequency detuned from the incident electromagnetic radiation, thereby providing an intermediate frequency difference signal.

19. The two-path plasmonic interferometer of claim 1, further comprising a sample in the source-side or drain-side plasmonic path.

20. The two-path plasmonic interferometer of claim 1, wherein the source-side and drain-side plasmonic path lengths are each shorter than a plasmon coherence length.

* * * * *